United States Patent
Pedrosa et al.

(10) Patent No.: US 9,326,956 B2
(45) Date of Patent: May 3, 2016

(54) METHODS FOR IMPROVING BRAIN DEVELOPMENT AND COGNITIVE FUNCTION USING BETA-HYDROXY-BETA METHYLBUTYRATE

(75) Inventors: Jose Maria Lopez Pedrosa, Granada (ES); Manuel Manzano Martin, Granada (ES); Alejandro Barranco Perez, Las Gabias (ES); Maria Ramirez Gonzalez, Granada (ES); Ricardo Rueda Cabrera, Granada (ES)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/984,906

(22) PCT Filed: Feb. 13, 2012

(86) PCT No.: PCT/US2012/024817
§ 371 (c)(1),
(2), (4) Date: Oct. 7, 2013

(87) PCT Pub. No.: WO2012/112419
PCT Pub. Date: Aug. 23, 2012

(65) Prior Publication Data
US 2014/0249223 A1   Sep. 4, 2014

Related U.S. Application Data

(60) Provisional application No. 61/443,762, filed on Feb. 17, 2011.

(51) Int. Cl.
| *A61K 31/19* | (2006.01) |
| *A23L 1/30* | (2006.01) |
| *A23L 1/305* | (2006.01) |
| *A23L 1/29* | (2006.01) |

(52) U.S. Cl.
CPC .............. *A61K 31/19* (2013.01); *A23L 1/296* (2013.01); *A23L 1/30* (2013.01); *A23L 1/3051* (2013.01); *A23V 2002/00* (2013.01)

(58) Field of Classification Search
CPC ..................................................... A61K 31/19
USPC ......................................................... 514/557
See application file for complete search history.

(56) References Cited

U.S. PATENT DOCUMENTS

| 6,291,525 | B1 | 9/2001 | Nissen |
| 8,217,077 | B2 | 7/2012 | Baxter |
| 8,778,992 | B2 | 7/2014 | Thomas |
| 2004/0071825 | A1 | 4/2004 | Lockwood |
| 2005/0027005 | A1 | 2/2005 | Boldt |
| 2005/0215640 | A1 | 9/2005 | Baxter et al. |
| 2006/0167075 | A1 | 7/2006 | Pearson et al. |
| 2007/0142469 | A1 | 6/2007 | Thomas |
| 2008/0317886 | A1 | 12/2008 | Sparkman |
| 2010/0179112 | A1 | 7/2010 | Rathmacher et al. |
| 2015/0238447 | A1 | 8/2015 | Sathyavageeswaran |

FOREIGN PATENT DOCUMENTS

| CN | 101785566 | 7/2010 |
| JP | 2009155336 A | 7/2009 |
| TW | 201117736 | 6/2011 |
| WO | 2006062424 A2 | 6/2006 |
| WO | 2009/116546 | 9/2009 |
| WO | 2010068696 | 6/2010 |
| WO | 2012088075 | 6/2012 |
| WO | 2012092035 | 7/2012 |
| WO | 2012112419 A1 | 8/2012 |
| WO | 2013142424 | 9/2013 |
| WO | 2014043685 | 3/2014 |

OTHER PUBLICATIONS

Rule 161 and 162 communication for EP App. No. 12705748.7 dated Mar. 6, 2014, 2 pages.
Office Action in VN 1-2013-02808 dated Dec. 20, 2013, 1 page.
International Search Report and Written Opinion for PCT/US2012/024817 dated Jun. 6, 2012 (6 pages).
International Preliminary Report on Patentability for PCT/US2012/024817 dated Aug. 21, 2013 (4 pages).
Extended Search Report for EP Application No. 12382531.7 dated Apr. 15, 2013 (4 pages).
Rule 161 and 162 communication for EP App. No. 12705748.7 dated Sep. 25, 2013 (2 pages).
Kuhls, et al., "Beta-hydroxy-beta-methylbutyrate supplementation in critically ill trauma patients," Journal of Trauma Injury Infection and Critical Care, vol. 62(1), pp. 125-132 (Jan. 2007).
English abstract for Japanese Patent No. 2009155336 Tsujido Chemical Corp.
Office Action in CA 2,825,734 dated Nov. 14, 2014 (4 pages).
First Office Action in CA 201280009207.4 dated Sep. 1, 2014 (8 pages).
Second Office Action in CN 201280009207.4 dated Feb. 4, 2015 (5 pages).
Search Report and Written Opinion in SG Application No. 2013062377 dated Aug. 12, 2014 (9 pages).

(Continued)

*Primary Examiner* — My-Chau T Tran
(74) *Attorney, Agent, or Firm* — Calfee, Halter & Griswold LLP

(57) ABSTRACT

Disclosed are methods for enhancing neural function in an individual, such as an older adult. The methods include administering nutritional compositions comprising HMB to the individual. The nutritional compositions provide benefits for individuals that have or may be at risk of having cognitive decline, cognitive impairment, and neural dysfunction, typically resulting from cognitive diseases associated with neurodegenerative diseases.

15 Claims, 7 Drawing Sheets

(56) References Cited

OTHER PUBLICATIONS

Burke et al., "Inhibition of mitogen-activated protein kinase and stimulation of Akt kinase signaling pathways: two approaches with therapeutic potential in the treatment of neurodegenerative disease," Pharmacology and Therapeutics, vol. 114, No. 3, pp. 261-277 (2007).

Kornasio et al., "B-hydroxy-B-methylbutyrate (Hmb) Stimulates Myogenic Cell Proliferation, Differentiation and Survival via the Mapk/Erk and P13K/Akt Pathways," Biochimica et Biophysica Acta, vol. 1793, No. 5, pp. 755-763 (2009).

Zeng Zhigang et al., "Physiological Efficacy of Supplemental Beta-hydroxy-beta-methylbutyrate (HMB) in Sports Training," Chinese Journal of Sports Medicine, vol. 26, No. 1 (Jan. 10, 2007), pp. 120-123.

Zhang et al., "The Pi3K/Akt Pathway Mediates the Neuroprotective Effect of Atovastatin in Extending Thrombolytic Therapy after Embolic Stroke in the Rat," Anterioscler Thromb Vasc Biol., vol. 27, pp. 2470-2475 (2007).

International Search Report, Written Opinion and Notification for PCTUS2013/060120 dated Nov. 15, 2013 (12 pages).

International Preliminary Report on Patentability for PCT/US2013/060120 dated Mar. 17, 2015 (7 pages).

Portal, Shawn et al., "Effect of HMB supplementation on body composition, fitness, hormonal profile and muscle damage indices," Journal of Pediatric Endocrinology and Metabolism, vol. 23, No. 7 (2010), pp. 641-650.

Rule 161 and 162 communication for EP App. No. 13766463.7 dated May 6, 2015 (2 pages).

Further Search Report and Written Opinion in SG Application No. 2013062377 dated Apr. 15, 2015 (6 pages).

"Disorders of the Nervous System" http://web.archive.org/web/20090616094835/http://www.dartmouth.edu/dons/figures/chapt_24/Table_24-2.htm (last accessed May 13, 2015) (2 pages).

Li et al., "Transcription factor MEF2C influences neural stem/progenitor cell differentiation and maturation in vivo," PNAS, Jul. 8, 2008, vol. 105, No. 27, pp. 9397-9402.

Morris, et al., "Mild Cognitive Impairment Represents Early-Stage Alzheimer Disease," Arch. Neurol., Mar. 2001, vol. 58(3), pp. 397-405.

English-language machine translation from Lexis Nexis of Chinese Patent No. 101785566 (8 pages).

English-language translation of Abstract from Espacenet—European Patent Office—of Taiwan Patent No. 201117736 (1 page).

English language abstract for Zeng Zhigang et al., "Physiological Efficacy of Supplemental Beta-hydroxy-beta-methylbutyrate (HMB) in Sports Training," Chinese Journal of Sports Medicine, vol. 26, No. 1 (Jan. 10, 2007), pp. 120-123 (1 page).

Office Action in U.S. Appl. No. 14/428,535 dated Sep. 3, 2015.

English translation of Office Action for JP Application No. 2013-554520 dated Jan. 19, 2016.

Final Examination Report for SG Application No. 2013062377 dated Jan. 26, 2016.

Search Report and Examination Report in SG Application No. 11201502069 dated Dec. 22, 2015 (Search Report dated Oct. 15, 2015 but received from foreign associate Dec. 22, 2015).

Van Weenen, De Leeuw, et al., "Pharmacological modulation of dopamine receptor D2-medicated transmissions alters the metabolic phenotype of diet induced obese and diet resistant C57B16 mice," Experimental Diabetes Research (2011), vol. 2011 pp. 1-10.

METHODS FOR IMPROVING BRAIN DEVELOPMENT AND COGNITIVE FUNCTION USING BETA-HYDROXY-BETA METHYLBUTYRATE

CROSS REFERENCE TO RELATED APPLICATIONS

This application is the U.S. national stage entry of PCT/US2012/024817, with an international filing date of 2012 Feb. 13, which is herein incorporated by reference in its entirety and which claims priority to and any other benefit of U.S. Provisional Application Ser. No. 61/443,762, with a filing date of 2011 Feb. 17, which is herein incorporated by reference in its entirety.

FIELD OF THE DISCLOSURE

The present disclosure relates to selected methods for enhancing neural development and cognitive function in adults and older adults by administering nutritional products comprising beta-hydroxy-beta methylbutyrate (HMB).

BACKGROUND OF THE DISCLOSURE

Manufactured nutritional liquids and powders comprising a targeted selection of nutrition ingredients are well known and widely available, some of which may provide a sole source of nutrition while others may provide a supplemental source. These nutritionals include powders that can be reconstituted with water or other aqueous liquid, as well as ready to drink nutritional liquids such as milk or protein based emulsions or non-emulsified liquids. These nutritional liquids are especially useful when formulated with selected nutritional ingredients.

One such nutritional ingredient is beta-hydroxy-beta-methylbutyrate (HMB). HMB is a naturally occurring amino acid metabolite of leucine that is known for use in a variety of nutritional products and supplements. HMB is known for use in such products to help build or maintain healthy muscle mass and strength in selected individuals.

Calcium HMB is a commonly used form of HMB when formulated into oral nutritional products, which products may include tablets, capsules, reconstitutable powders, nutritional liquids and emulsions. Some of these HMB-containing products contain additional nutrients such as fat, carbohydrate, protein, vitamins, minerals and so forth.

Recently, there has been increased interest in designing and marketing so-called "smart formulations" that include nutritional products designed specifically for brain health and nourishment. Many of these products are specifically designed for improving cognition and preventing dementia and related cognitive-decline conditions and diseases. To date, these formulations and products have had limited success.

As such, there is a need for compositions and methods for easily and effectively improving cognition generally, and treating cognitive decline, cognitive impairment, and cognitive disease specifically. Additionally, it would be beneficial if the compositions and methods could be used by a wide variety of individuals, and particularly older adults, irrespective of overall health and physical status.

SUMMARY OF THE DISCLOSURE

The present disclosure is directed to methods of improving cognitive function and/or preventing/treating/reducing cognitive decline, cognitive impairment, and cognitive disease in individuals, and in particular, in older adults. The methods include administering to an individual an effective amount of HMB.

One embodiment is directed to a method for improving cognition in an older adult. The method comprises administering to the older adult a composition including an amount of HMB effective to improve cognition in the older adult.

Another embodiment is directed to a method for treating a cognitive disease associated with a neurodegenerative disease in an older adult. The method comprises administering to the older adult a composition including an amount of HMB effective to treat the cognitive disease in the older adult. The neurodegenerative disease may include, for example, Alzheimer's disease, Huntington's disease, Parkinson's disease, dementia, amyotrophic lateral sclerosis, stroke, and schizophrenia.

Another embodiment is directed to a method of improving cognitive function in a toddler, child or adolescent. The method comprises administering to the toddler, child, or adolescent a composition including an amount of HMB effective to improve cognitive function in the toddler, child or adolescent.

The methods described herein may provide protection to the brain and neural tissue in individuals and may protect the brain and neural tissues from deterioration, thereby preventing and/or treating cognitive diseases associated with neurodegenerative diseases, particularly in older adults. Additionally, by providing neuroprotection to the brain, neural function may be enhanced by administration of a nutritional product including HMB.

Other components for use in the nutritional compositions and supplements can be included with the HMB. For example, in one or more embodiments, the composition may include at least one of a protein, a carbohydrate, a fat, vitamins and minerals.

DETAILED DESCRIPTION OF THE DISCLOSURE

Figure 1:
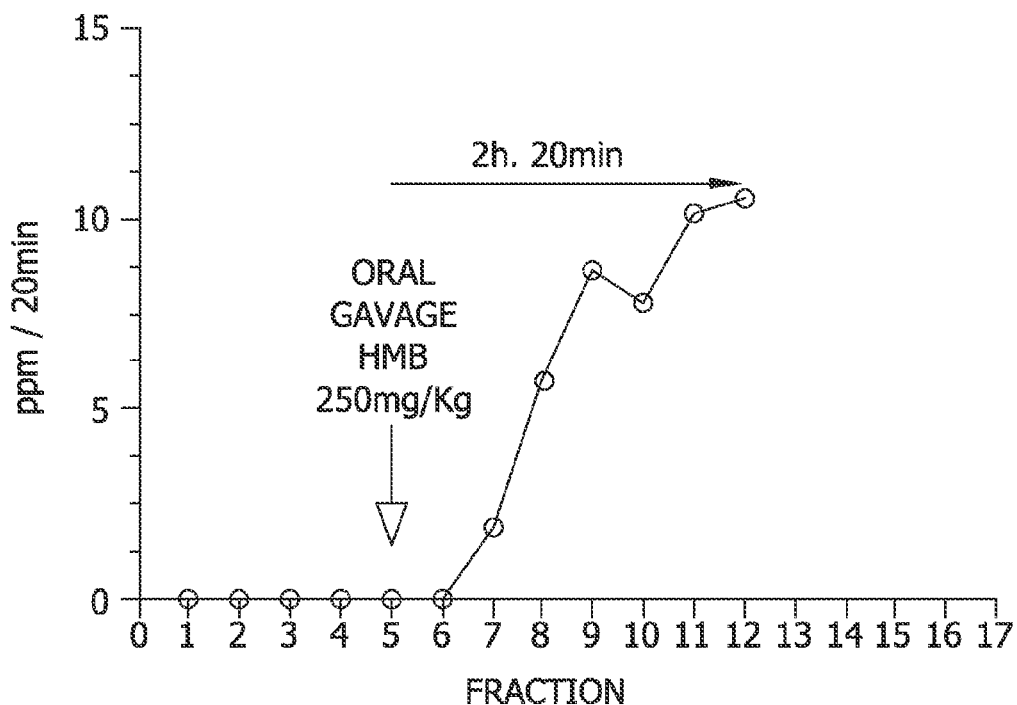
FIG. 1 is a graph depicting time-course concentration of HMB in brain microdyalisates of rat 1 as evaluated in Example 11.

The methods of the present disclosure are directed to utilizing HMB-containing compositions to improve cognitive function and reduce cognitive decline, cognitive impairment, and cognitive disease, particularly in older adults. These and other essential or optional elements or limitations of the methods of the present disclosure are described in detail hereafter.

The term "older adult" as used herein, unless otherwise specified, refers to an individual of at least 45 years of age, including at least 50 years of age, including at least 55 years of age, including at least 60 years of age, including at least 65 years of age, including at least 70 years of age, including at least 75 years of age, including at least 80 years of age or greater, and also including from about 45 years of age to about 80 years of age, further including from about 55 years of age to about 80 years of age.

The term "calcium HMB" as used herein, unless otherwise specified, refers to the calcium salt of beta-hydroxy-beta-methylbutyrate (also referred to as beta-hydroxyl-methyl butyric acid, beta-hydroxy isovaleric acid, or HMB), which is most typically in a monohydrate form. All weights, percentages, and concentrations as used herein to characterize calcium HMB are based on the weight of calcium HMB monohydrate, unless otherwise specified.

The term "spray dried powder" as used herein, unless otherwise specified, refers to a nutritional powder wherein the majority of the components, including HMB, have been homogenized and subsequently subjected to a spray drying process during manufacturing. Additional ingredients can be added to the spray dried powder through dryblending so long as at least the HMB has been previously homogenized and spray dried.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "shelf stable" as used herein, unless otherwise specified, refers to a nutritional liquid that remains commercially stable after being packaged and then stored at 18-24° C. for at least 3 months, including from about 6 months to about 24 months, and also including from about 12 months to about 18 months.

The term "neural function" as used herein, unless otherwise specified, refers to the functioning of brain and neuronal tissue to support and maintain cognitive abilities, e.g., learning and memory. By contrast, the term "neural dysfunction" as used herein, unless otherwise specified, refers to reduced memory or cognitive function. For example, a reduced learning ability or ability to recall information is considered neural dysfunction. Neural dysfunction in some embodiments may be the result of aging or neurodegenerative disease.

The term "neuroprotection" as used herein, unless otherwise specified, refers to the protection of existing neurons and neural tissue from apoptosis or degeneration; protection of existing neurons and neural tissue against physical injury; and stimulating neuronal regeneration.

The term "cognition" as used herein, unless otherwise specified, refers to the mental processes involved in gaining knowledge and comprehension, including thinking, knowing, remembering, judging and problem solving. "Cognition" includes higher-level functions of the brain and encompasses language, imagination, perception, and planning.

The terms "nutritional composition" or "nutritional product" as used herein, unless otherwise specified, refer to nutritional liquids and nutritional powders, the latter of which may be reconstituted to form a nutritional liquid, all of which comprise HMB and one or more of fat, protein and carbohydrate and are suitable for oral consumption by a human.

The term "nutritional liquid" as used herein, unless otherwise specified, refers to nutritional products in ready-to-drink liquid form and to nutritional liquids made by reconstituting the nutritional powders described herein prior to use.

The term "substantially clear liquid" as used herein, unless otherwise specified, refers to nutritional liquids that are substantially fat free; that is, the liquids are devoid of added fat except for that fat inherent to the raw materials or added fat at low concentrations to aid in the manufacture of the liquid. In this context, the term "fat free" means that the liquid typically contains less than 1.0%, more typically less than 0.5%, and more typically less than 0.1%, including zero percent, fat by weight of the nutritional liquid. These substantially clear nutritional liquids are flowable or drinkable liquids at from about 1 to about 25° C.

All percentages, parts and ratios as used herein, are by weight of the total composition, unless otherwise specified. All such weights as they pertain to listed ingredients are based on the active level and, therefore, do not include solvents or byproducts that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the nutritional compositions of the present disclosure may also be substantially free of any optional or selected essential ingredient or feature described herein, provided that the remaining nutritional product still contains all of the required ingredients or features as described herein. In this context, and unless otherwise specified, the term "substantially free" means that the selected nutritional product contains less than a functional amount of the optional ingredient, typically less than 1%, including less than 0.5%, including less than 0.1%, and also including zero percent, by weight of such optional or selected essential ingredient.

The nutritional compositions and methods described herein may comprise, consist of, or consist essentially of the essential elements of the compositions and methods as described herein, as well as any additional or optional elements described herein or otherwise useful in nutritional product applications.

Product Form

The compositions including the HMB useful in the methods of the present disclosure may be formulated in any known or otherwise suitable product form for oral or parenteral administration. Oral product forms are generally preferred and include any solid, liquid, or powder formulation suitable for use herein, provided that such a formulation allows for safe and effective oral delivery of the essential and other selected ingredients from the selected product form.

Non-limiting examples of solid nutritional product forms suitable for use herein include snack and meal replacement products, including those formulated as bars, sticks, cookies or breads or cakes or other baked goods, frozen liquids, candy, breakfast cereals, powders or granulated solids or other particulates, snack chips or bites, frozen or retorted entrees and so forth.

Non-limiting examples of liquid product forms suitable for use herein include snack and meal replacement products, hot or cold beverages, carbonated or non carbonated beverages, juices or other acidified beverages, milk or soy-based beverages, shakes, coffees, teas, enteral feeding compositions, and so forth. These liquid compositions are most typically formulated as suspensions or emulsions, but can also be formulated in any other suitable forms such as clear liquids, substantially clear liquids, solutions, liquid gels, and so forth.

Other non-limiting examples of suitable oral product forms include semisolid or semi-liquid compositions (e.g., puddings, gels), as well as more conventional product forms such as capsules, tablets, caplets, pills, and so forth. The quantity of the composition for providing an effective amount of HMB to the targeted user may be contained in one or a plurality of individual dosage forms, e.g., in one tablet or a plurality of tablets that may be administered in single or multiple dosages per day.

For product forms such as lozenges, tablets (e.g. chewable, coated, etc.), pastes, or gels, the amino acid blend may be formulated at concentrations most typically ranging from about 5 to about 50%, including from about 15 to about 33%, and also including from about 15 to about 25%, by weight of the product form, all in combination with excipients or other ingredients such as carbohydrates, acidulants, flavors, and colors.

The compositions including HMB may be formulated with sufficient kinds and amounts of nutrients to provide a sole, primary, or supplemental source of nutrition, or to provide a specialized nutritional product for use in individuals afflicted with specific diseases or conditions or with a targeted nutritional benefit.

Beta-Hydroxy-Beta-Methylbutyrate (HMB)

The compositions for use in the methods of the present disclosure comprise HMB, which means that the compositions are either formulated with the addition of HMB, most typically as a calcium monohydrate, or are otherwise prepared so as to contain calcium and HMB in the finished product. Any source of HMB is suitable for use herein provided that the finished product contains HMB, although such a source is preferably calcium HMB and is most typically added as such to the compositions during formulation.

The term "added calcium HMB" as used herein means a calcium salt of HMB, most typically as monohydrate calcium salt of HMB, as the HMB source added to the nutritional product.

Although calcium HMB monohydrate is the preferred source of HMB for use herein, other suitable sources may include HMB as the free acid, a salt, an anhydrous salt, an ester, a lactone, or other product forms that otherwise provide a bioavailable form of HMB from the nutritional product. Non-limiting examples of suitable salts of HMB for use herein include HMB salts, hydrated or anhydrous, of sodium, potassium, magnesium, chromium, calcium, or other non-toxic salt form. Calcium HMB monohydrate is preferred and is commercially available from Technical Sourcing International (TSI) of Salt Lake City, Utah.

The concentration of HMB in nutritional liquid compositions suitable for use in the methods may range up to 10%, including from about 0.01% to 10%, and also including from about 0.1% to about 5.0%, and also including from about 0.5% to about 2.0%, and also including from about 0.4% to about 1.5%, by weight of the nutritional liquid composition. In one specific embodiment, the HMB is present in the nutritional liquid composition in an amount of about 0.67%, by weight of the nutritional liquid composition.

The concentration of HMB in the nutritional solid compositions suitable for use in the methods may range up to 10%, including from about 0.01% to 10%, and also including from about 0.1% to about 7.0%, and also including from about 1.0% to about 5.0%, and also including from about 1.0% to about 4.0%, by weight of the nutritional solid composition. In one specific embodiment, the HMB is present in the nutritional solid in an amount of about 3.2%, by weight of the nutritional solid composition.

The nutritional compositions administered to the individuals as described herein may provide from about 0.1 to about 10 grams/day of HMB, including from about 0.1 to about 5.0 grams/day of HMB. Accordingly, the nutritional compositions may provide from about 0.5 to about 2.5 grams, including from about 1.0 to about 1.7 grams, including about 1.5 grams of HMB per serving, wherein a serving may be about 240 ml of ready to feed nutritional liquid or about 240 ml of reconstituted nutritional solid. In one specific embodiment, HMB is provided at a level of about 1.58 grams per 240 ml. The individual may be administered one serving per day, two servings per day, three servings per day, or four or more servings per day to receive the desired amount of HMB from the nutritional composition.

Macronutrients

The compositions as disclosed herein including HMB for use in the methods may further comprise one or more other macronutrients including a fat source, a carbohydrate source, and a protein source, all in addition to the HMB as described herein.

The optional macronutrients in combination with the other essential or added ingredients may provide up to 1000 kcal of energy per serving or dose, including from about 25 kcal to about 900 kcal, also including from about 75 kcal to about 700 kcal, also including from about 100 kcal to about 500 kcal, also including from about 150 kcal to about 400 kcal, and also including from about 200 kcal to about 300 kcal, per serving or dose, most suitably as a single, undivided serving or dose.

Many different sources and types of proteins, lipids, and carbohydrates are known and can be used in the HMB-containing compositions as described herein, provided that the selected nutrients are safe and effective for oral administration and are compatible with the essential and other added ingredients.

Carbohydrates suitable for use in the compositions may be simple, complex, or variations or combinations thereof. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, indigestible oligosaccharides (e.g., fructooligosaccharides), soluble or insoluble fiber, honey, sugar alcohols (e.g., maltitol, erythritol, sorbitol), and combinations thereof.

Proteins suitable for use in the compositions, in addition to the HMB component as described herein, include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof.

Fats suitable for use in the compositions include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oil, cottonseed oil, and combinations thereof.

The concentration or amount of fat, protein, and carbohydrate in the compositions of the present disclosure may vary considerably depending upon the particular product form (e.g., solid, liquid, powder) and the various other formulations and targeted dietary needs. These macronutrients are most typically formulated within any of the caloric ranges (embodiments A-D) described in the following table.

| Nutrient (% Calories) | Embodiment A | Embodiment B | Embodiment C | Embodiment D |
| --- | --- | --- | --- | --- |
| Carbohydrate | 0-98 | 2-96 | 10-75 | 30-50 |
| Fat | 0-98 | 2-96 | 20-85 | 35-55 |
| Protein | 0-98 | 2-96 | 5-70 | 15-35 |

* Each numerical value is preceded by the term "about"

Optional Ingredients

The nutritional compositions comprising the HMB may further comprise other optional ingredients that may modify the physical, nutritional, chemical, hedonic or processing characteristics of the products or serve as pharmaceutical or additional nutritional components when used in the targeted population. Many such optional ingredients are known or otherwise suitable for use in other nutritional compositions and may also be used in the nutritional compositions described herein, provided that such optional ingredients are safe and effective for oral administration and are compatible with the essential and other ingredients in the selected product form.

Non-limiting examples of such optional ingredients include preservatives, antioxidants, emulsifying agents, buffers, fructooligosaccharides, chromium picolinate, pharmaceutical actives, additional nutrients as described herein, colorants, flavors, thickening agents and stabilizers, and so forth.

The compositions may further comprise vitamins or related nutrients, non-limiting examples of which include vitamin A, vitamin D, vitamin E, vitamin K, thiamine, riboflavin, pyridoxine, vitamin B12, carotenoids, niacin, folic acid, pantothenic acid, biotin, vitamin C, choline, inositol, salts, and derivatives thereof, and combinations thereof.

The compositions may further comprise minerals, non-limiting examples of which include phosphorus, magnesium, calcium, iron, zinc, manganese, copper, sodium, potassium, molybdenum, chromium, selenium, chloride, and combinations thereof.

The compositions may also include one or more flavoring or masking agents. Suitable flavoring or masking agents include natural and artificial sweeteners, sodium sources such as sodium chloride, and hydrocolloids, such as guar gum, xanthan gum, carrageenan, gellan gum, gum acacia and combinations thereof.

Methods of Manufacture

The HMB-containing nutritional liquid compositions may be manufactured by any known or otherwise suitable method for making nutritional liquids, including emulsions such as milk-based nutritional emulsions.

In one suitable manufacturing process, a nutritional liquid is prepared using at least three separate slurries, including a protein-in-fat (PIF) slurry, a carbohydrate-mineral (CHO-MN) slurry, and a protein-in-water (PIW) slurry. The PIF slurry is formed by heating and mixing the selected oils (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. Avicel, gellan, carrageenan), and HMB. The resulting CHO-MIN slurry is held for 10 minutes with continued heat and agitation before adding additional minerals (e.g., potassium chloride, magnesium carbonate, potassium iodide, etc.) and/or carbohydrates (e.g., fructooligosaccharide, sucrose, corn syrup, etc.). The PIW slurry is then formed by mixing with heat and agitation the remaining protein (e.g., sodium caseinate, soy protein concentrate, etc.) into water.

The resulting slurries are then blended together with heated agitation and the pH adjusted to the desired range, typically from 6.6-7.0, after which the composition is subjected to high-temperature short-time (HTST) processing during which the composition is heat treated, emulsified and homogenized, and then allowed to cool. Water soluble vitamins and ascorbic acid are added, the pH is again adjusted to the desired range if necessary, flavors are added, and water is added to achieve the desired total solid level. The composition is then aseptically packaged to form an aseptically packaged nutritional emulsion, or the composition is added to retort stable containers and then subjected to retort sterilization to form retort sterilized nutritional emulsions.

The manufacturing processes for the nutritional emulsions may be carried out in ways other than those set forth herein without departing from the spirit and scope of the present disclosure. The present embodiments are, therefore, to be considered in all respects illustrative and not restrictive and that all changes and equivalents also come within the description of the present disclosure.

The nutritional solid, such as a spray dried nutritional powder, may be prepared by any collection of known or otherwise effective techniques, suitable for making and formulating a spray dried nutritional powder.

The spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising HMB, and optionally protein, carbohydrate, and fat, and then spray drying the slurry or liquid to produce a spray dried nutritional powder. The method may further comprise the step of spray drying, dry mixing, or otherwise adding additional nutritional ingredients, including any one or more of the ingredients described herein, to the spray dried nutritional powder.

The methods of manufacture are preferably formulated with calcium HMB, which is most typically formulated as calcium HMB monohydrate, as the HMB source for use in the methods.

Methods of Use

The compositions including HMB as described herein may be administered to individuals generally, including adults, older adults, toddlers, children and adolescents, specifically, to improve cognition generally, or to treat a specific cognitive disease or condition, such as a cognitive disease associated with a neurodegenerative disease in an older adult. The individual may be generally healthy, or may suffer from (or be at risk of suffering from) cognitive decline, cognitive impairment (including mild cognitive impairment (MCI)), memory lapses, general recall issues, cognitive disorders, or a neurodegenerative disease such as Alzheimer's disease, Huntington's disease, Parkinson's disease, dementia, amyotrophic lateral sclerosis, stroke, and schizophrenia. With respect to toddlers, children, and adolescents specifically, the HMB-containing compositions may improve overall cognitive function and brain development.

The HMB-containing nutritional compositions enhance neural function in individuals, including older adults who may benefit substantially from the enhanced neural function, as neural function generally decreases with age. Specifically, older adults who suffer from neural dysfunction may particularly benefit from the HMB-containing compositions.

In specific embodiments, the individual receiving the HMB-containing composition may be an older adult who has or who is at risk of developing a cognitive disorder or at risk of developing cognitive decline or a cognitive impairment (including MCI). Individuals who are "at risk" of developing cognitive decline or a cognitive disorder or impairment include individuals who have a specific form of a gene referred to as APOE-e4, hypertension, diabetes mellitus, depression, high blood pressure, elevated cholesterol, and/or family history of cognitive decline, cognitive impairment, and/or cognitive disorder/disease due to age.

The methods described herein utilizing the HMB-containing compositions are further directed to providing the individual upon administration of such compositions, most typically after daily use over an extended period of time of from about 1 month to about 10 years, including from about 1 month to about 1 year, and further including about 1 month to about 6 months, one or more of: (1) support and maintenance of neural function of adults and older adults; (2) enhanced neural function in adults and older adults; (3) neuroprotection to adults and older adults; (4) cognitive disease prevention/treatment associated with a neurodegenerative disease in adults and older adults; (5) cognitive decline or cognitive impairment prevention/treatment in adults and older adults; and (6) improved cognitive ability of toddlers, children and adolescents. In one embodiment, the HMB-containing compositions are administered daily for a period of at least one year.

The nutritional products may be administered orally as needed to provide the desired level of nutrition, most typically in the form of one to two servings daily, in one or two or more divided doses daily, e.g., serving sizes typically ranging from about 100 to about 300 ml, including from about 150 to about 250 ml, and including from about 190 ml to about 240 ml.

EXAMPLES

The following examples illustrate specific embodiments and or features of the HMB-containing nutritional compositions and the methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified HMB-containing compositions are nutritional products prepared in accordance with manufacturing methods well known in the nutrition industry for preparing nutritional emulsions and spray dried nutritional powders.

Examples 1-5

Examples 1-5 illustrate spray dried nutritional HMB-containing powders suitable for use in the methods of the present disclosure, the ingredients of which are listed in the table below. These products are prepared by spray drying methods in separate batches and are reconstituted with water prior to use to the desired target ingredient concentrations. All ingredient amounts are listed as kilogram per 1000 kilogram batch of product, unless otherwise specified.

| Ingredient | Ex. 1 | Ex. 2 | Ex. 3 | Ex. 4 | Ex. 5 |
| --- | --- | --- | --- | --- | --- |
| Maltodextrin | 436.7 | 436.7 | 436.7 | 436.7 | 436.7 |
| Sucrose | 145.5 | 145.5 | 145.5 | 145.5 | 145.5 |
| Calcium Caseinate | 129.1 | 129.1 | 129.1 | 129.1 | 129.1 |
| Isolated Soy Protein | 57.7 | 57.7 | 57.7 | 61.7 | 57.7 |
| FOS Powder | 33.6 | 33.6 | 33.6 | 33.6 | 32.6 |
| HO sunflower oil | 59.9 | 55.5 | 61.24 | 57.2 | 62.58 |
| Calcium HMB | 31.6 | 34.6 | 28.6 | 27.6 | 32.6 |
| Canola Oil | 55.1 | 53.7 | 56.4 | 52.42 | 57.78 |
| Soy Oil | 26.7 | 26.0 | 27.37 | 25.36 | 28.04 |
| Potassium Citrate | 10.3 | 10.3 | 10.3 | 10.3 | 10.3 |
| Sodium Citrate | 5.8 | 5.8 | 5.8 | 5.8 | 5.8 |
| Potassium Chloride | 5.2 | 5.2 | 5.2 | 5.2 | 5.2 |
| Magnesium Chloride | 4.7 | 4.7 | 4.7 | 4.7 | 4.7 |
| Potassium hydroxide | 3.1 | 3.1 | 3.1 | 3.1 | 3.1 |
| Sodium phosphate dibasic dihydrate | 3.0 | 3.0 | 3.0 | 3.0 | 3.0 |
| Sodium chloride | 2.5 | 2.5 | 2.5 | 2.5 | 2.5 |
| Choline Chloride | 1.8 | 1.8 | 1.8 | 1.8 | 1.8 |
| Flavor | 1.8 | 1.8 | 1.8 | 1.8 | 1.8 |
| Sodium phosphate monobasic monohydrate | 1.6 | 1.6 | 1.6 | 1.6 | 1.6 |
| Potassium phosphate dibasic trihydrate | 1.1 | 1.1 | 1.1 | 1.1 | 1.1 |
| Flavor | 1.0 | 1.0 | 1.0 | 1.0 | 1.0 |
| Vitamin premix | 1.0 | 1.0 | 1.0 | 1.0 | 1.0 |
| Ascorbyl palmitate | 0.243 | 0.243 | 0.243 | 0.243 | 0.243 |
| Ascorbic acid | 0.240 | 0.240 | 0.240 | 0.240 | 0.240 |
| Antioxidant | 0.116 | 0.116 | 0.116 | 0.116 | 0.116 |
| Ferrous sulfate | 0.092 | 0.092 | 0.092 | 0.092 | 0.092 |
| Vitamin premix | 0.065 | 0.065 | 0.065 | 0.065 | 0.065 |
| Zinc sulfate monohydrate | 0.057 | 0.057 | 0.057 | 0.057 | 0.057 |
| Manganese sulfate | 0.045 | 0.045 | 0.045 | 0.045 | 0.045 |

-continued

| Ingredient | Ex. 1 | Ex. 2 | Ex. 3 | Ex. 4 | Ex. 5 |
|---|---|---|---|---|---|
| Mineral mix copper sulfate | 0.035 | 0.035 | 0.035 | 0.035 | 0.035 |
| Beta carotene | 0.005 | 0.005 | 0.005 | 0.005 | 0.005 |
| Chromium chloride | 0.001 | 0.001 | 0.001 | 0.001 | 0.001 |
| Sodium molybdate | 0.0012 | 0.0012 | 0.0012 | 0.0012 | 0.0012 |
| Potassium iodide | 0.001 | 0.001 | 0.001 | 0.001 | 0.001 |
| Sodium selenite | 0.0004 | 0.0004 | 0.0004 | 0.0004 | 0.0004 |
| Citric acid | AN | AN | AN | AN | AN |
| Potassium hydroxide | AN | AN | AN | AN | AN |
| Magnesium sulfate dry | AN | AN | AN | AN | AN |
| Ultra micronized tricalcium phosphate | AN | AN | AN | AN | AN |
| Ascorbic acid | AN | AN | AN | AN | AN |

AN = As Needed

Examples 6-10

Examples 6-10 illustrate HMB-containing nutritional emulsion embodiments of the present disclosure, the ingredients of which are listed in the table below. All amounts are listed as kilogram per 1000 kilogram batch of product, unless otherwise specified.

| Ingredient | Ex. 6 | Ex. 7 | Ex. 8 | Ex. 9 | Ex. 10 |
|---|---|---|---|---|---|
| Water | Q.S. | Q.S. | Q.S. | Q.S. | Q.S. |
| Sucrose | 89.3 | 89.3 | 89.3 | 89.3 | 89.3 |
| Maltodextrin | 29.7 | 29.7 | 29.7 | 29.7 | 29.7 |
| Sodium Caseinate | 25.9 | 25.9 | 25.9 | 25.9 | 25.9 |
| Milk Protein Caseinate | 19.1 | 19.1 | 19.1 | 19.1 | 19.1 |
| Soy Protein Isolate | 11.9 | 11.9 | 9.9 | 12.9 | 13.9 |
| Potassium Citrate | 7.9 | 7.9 | 7.9 | 7.9 | 7.9 |
| Soy Oil | 11.1 | 9.9 | 11.4 | 10.7 | 11.6 |
| Calcium HMB | 6.7 | 7.7 | 8.7 | 5.7 | 4.7 |
| Canola Oil | 10.2 | 10.0 | 10.5 | 9.8 | 10.7 |
| Corn Oil | 9.3 | 9.1 | 9.6 | 8.9 | 9.8 |
| Whey Protein Concentrate | 3.5 | 3.5 | 3.5 | 3.5 | 3.5 |
| Magnesium Phosphate Dibasic | 3.1 | 3.1 | 3.1 | 3.1 | 3.1 |
| Flavoring | 2.0 | 2.0 | 2.0 | 2.0 | 2.0 |
| Microcrystalline Cellulose | 2.0 | 2.0 | 2.0 | 2.0 | 2.0 |
| Soy Lecithin | 1.5 | 1.5 | 1.5 | 1.5 | 1.5 |
| Sodium Phosphate Dibasic Dihydrate | 1.3 | 1.3 | 1.3 | 1.3 | 1.3 |
| Potassium Phosphate Dibasic | 0.985 | 0.985 | 0.985 | 0.985 | 0.985 |
| Potassium Chloride | 0.729 | 0.729 | 0.729 | 0.729 | 0.729 |
| Choline Chloride | 0.480 | 0.480 | 0.480 | 0.480 | 0.480 |
| Ascorbic Acid | 0.469 | 0.469 | 0.469 | 0.469 | 0.469 |
| Calcium Carbonate | 0.451 | 0.451 | 0.451 | 0.451 | 0.451 |
| Flavor | 0.450 | 0.450 | 0.450 | 0.450 | 0.450 |
| N&A Dairy Cream | 0.450 | 0.450 | 0.450 | 0.450 | 0.450 |
| UTM/TM Premix | 0.367 | 0.367 | 0.367 | 0.367 | 0.367 |
| 45% Potassium Hydroxide | 0.323 | 0.323 | 0.323 | 0.323 | 0.323 |
| Carrageenan | 0.200 | 0.200 | 0.200 | 0.200 | 0.200 |
| Water Soluble Vitamin Premix | 0.185 | 0.185 | 0.185 | 0.185 | 0.185 |
| Vitamin DEK Premix | 0.067 | 0.067 | 0.067 | 0.067 | 0.067 |
| Sodium Chloride | 0.060 | 0.060 | 0.060 | 0.060 | 0.060 |
| Gellan Gum | 0.050 | 0.050 | 0.050 | 0.050 | 0.050 |
| Vitamin A Palmitate | 0.0082 | 0.0082 | 0.0082 | 0.0082 | 0.0082 |
| Corn oil carrier | Q.S. | Q.S. | Q.S. | Q.S. | Q.S. |
| Vitamin $D_3$ | 399 mg | 399 mg | 399 mg | 399 mg | 399 mg |
| Potassium Iodide | 194 mg | 194 mg | 194 mg | 194 mg | 194 mg |

Example 11

In this Example, the appearance of HMB and its concentration over time in brain interstitial fluid were analyzed after oral administration of HMB.

Initially, Sprague-Dawley rats (Charles River, France) weighing 400-500 g were housed in cages at constant room temperature (22±2° C.) and 45-55% humidity under a regular 12-hour light/dark schedule. Food and water were freely available. Procedures involving animals and their care were conducted in conformity with the institutional guidelines that are in compliance with national laws and EC policies for the Care and Use of Laboratory Animals (RD 2101-2005, 86/609/CEE).

A guide cannula was stereotaxically inserted into the hippocampus area of each anesthetized rat at the coordinates described in a stereotaxic atlas for rats. The rats were allowed to recover from surgery for at least three days. On the first day of the experiment, a brain microdialysis probe (MD-2204, BR-4, 4 mm membrane, available from BASi, West Lafayette, Ind.) was inserted into the guide cannula of each rat. The probe was perfused with Ringer's solution (aCFS Harvard apparatus, #597316) at a constant rate of 2 µl/min. The rat was left in the cage with space for relatively free movement. Samples of dialysate were automatically collected every twenty minutes. A bolus dose of HMB (250 mg/kg body weight) was given by gavage 100 min after starting the experiment and sampling was continued for another 160-220 min.

HMB was measured using UPLC-MS. Specifically, samples of 30-40 µl in aCSF were microfiltered through a 0.2 µm nylon filter, diluted with an equal amount of water, and then injected into the UPLC-TQD (Acuity-TQD system available from Waters Corporation, Milford, Mass.). HMB was analyzed using a BEH Hillic column 1.7 µm; 2.1×150 mm using a gradient consisting of $H_2O$:MeCN 0.1% formic acid. The mass spectrometer was set to Ion Mode ES+.

Two rats were assayed on different days. The gavage was given at fraction 5. As shown in FIG. 1, HMB appeared in the brain of rat 1 40 minutes after administration (fraction 7), and increased sharply thereafter. The fractions were taken until more than 2.5 hours after the gavage. At that time, the HMB concentration level had not decreased. The maximum concentration of HMB measured was 10.5 ppm.

Figure 2:
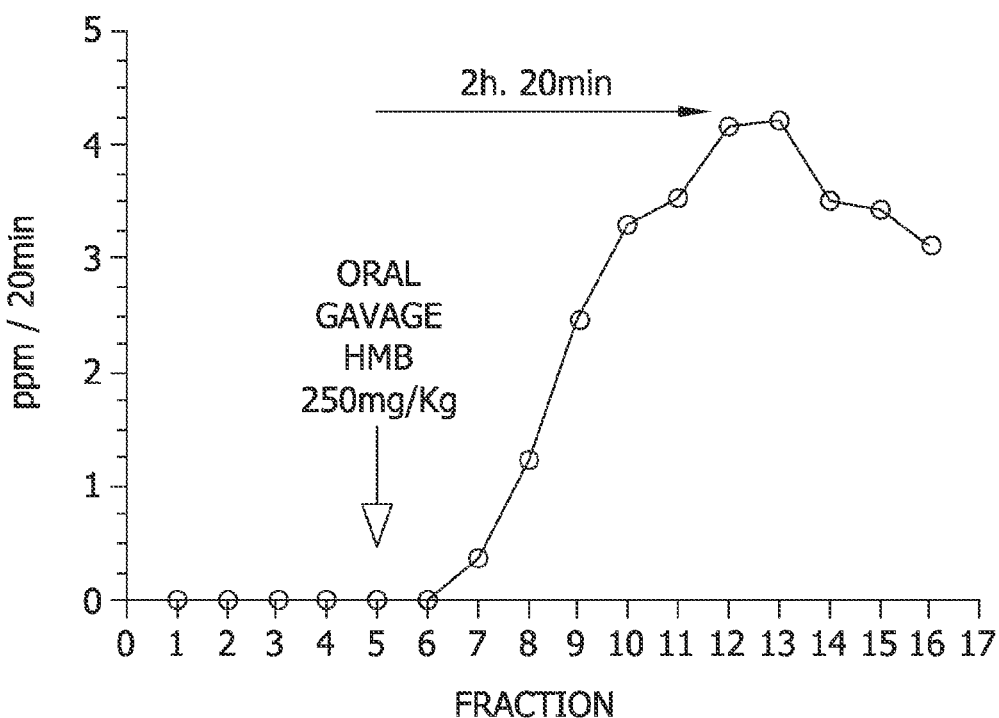
FIG. 2 is a graph depicting time-course concentration of HMB in brain microdyalisates of rat 2 as evaluated in Example 11.

FIG. 2 shows the results of rat 2. This time, the fractions were taken for a longer period to detect HMB concentration decrease. The time-course concentration of HMB in brain microdialysates of rat 2 followed a similar pattern as in rat 1. It was detected for the first time in fraction 7 and increased sharply for 2 h and 20 min after the administration (fractions 12-13), where the maximum concentration was reached (more than 4 ppm). HMB concentration level decreased thereafter, although at the end of the experiment (more than 3.5 h after the gavage), it had not yet reached basal level.

According to the results, HMB administered orally appears in brain interstitial fluids, which means that, despite its relatively hydrophilic properties, HMB was able to cross the blood brain barrier in a experimental model of microdialysis in rats.

Example 12

In this Example, the effects of HMB on the regulation of signaling cascades related to protein synthesis and cell proliferation in neural cells (Neuro 2A) was analyzed. Particularly, the effects of HMB as a nutritional component to induce neuronal development and plasticity and to confer neuroprotection were analyzed.

Neuronal development and synaptic transmission are plastic processes that are influenced by changing extracellular and intracellular conditions. Protein kinases are crucial for regulation of these phenomena and several of them (e.g., mitogen-activated protein kinases (ERK), phosphoinositide-3' kinase/AKT (PI3K/AKT) and calcium/calmodulin-dependent kinases (CaMKs)) have well-established roles in both neuronal development and synaptic plasticity. Recently, there has been growing interest in the serine/threonine protein kinase, mammalian target of rapamycin (mTOR). In fact, mTOR has a crucial role as regulator of different stages of neuronal development as well as in axon guidance, dendritic spine morphogenesis, and several forms of long-term synaptic plasticity.

Myocyte-enhancer factor 2 (MEF2) also plays an important role in neuronal survival. Pathways that regulate MEF2 activity in neuronal survival include p38 MAPK (ERK) and PI3-AKT phosphorylation upon the stimulation by either hormones/factors or membrane depolarization. Furthermore, in neurodegenerative diseases, macroautophagy is strongly induced by either degradation of MEF2 or suppression of the mTOR pathway, leading to neuronal death. Although the mechanism by which mTOR regulates MEF2 is unknown, several observations have pointed out that combined signaling through mTORC2 and AKT/PKB may be required for MEF2-triggered neuronal survival machinery.

For the transfection experiments in this Example, Neuro-2A cells were used at 80-90% confluence grown in Dulbecco's Modified Eagle's medium (DMEM). Cells were exposed for 5 hours to plasmid pGL3-4×MEF, which contains 4 copies in tandem of the MEF2D binding DNA sequence prior to the sequence of DNA which codes for firefly luciferase. Effectors were added to the medium for 18 h and luciferase activity was determined. For the study of inhibition of signaling factors, inhibitors of the phosphatidyl-inositol 3 kinase (LY294002), ERK 1/2 (PD98059) and mTORC1 activations (rapamycin) were added to the cells.

The effect of HMB on the rate of protein synthesis in Neuro-2A cells was determined by measuring the incorporation of [3H]-tyrosine into cellular protein pool. The phosphorylative status of mTOR and up/down-protein kinases (Akt, ERK 1/2) was determined by western blot. The cell proliferation/viability was determined with the MTT (3-(4,5-dimethylthiazol-2-yl)-2,5-diphenyltetrazolium bromide) colorimetric assay.

Data are expressed as mean±SEM. Student t-test was used to analyze the results.

Figure 3A:
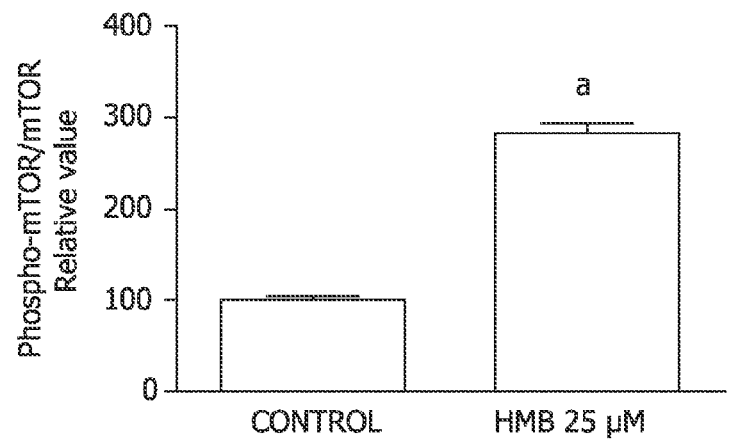
FIG. 3A is a graph depicting the effect of HMB on phosphorylative status of mTOR in Neuro 2A cells as evaluated in Example 12.
Figure 3B:
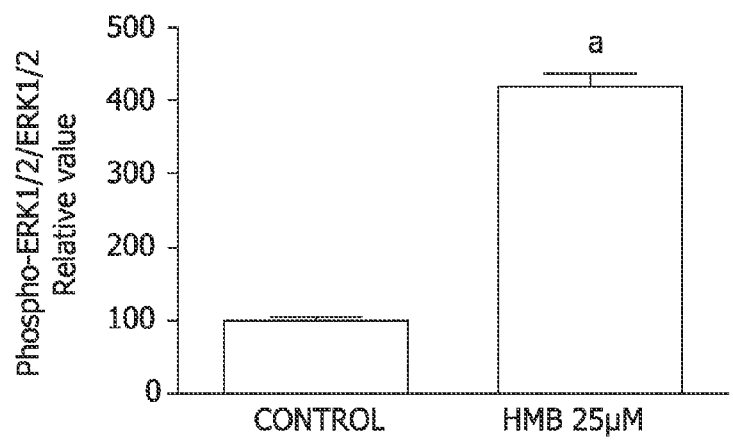
FIG. 3B is a graph depicting the effect of HMB on phosphorylative status of ERK1/2 in Neuro 2A cells as evaluated in Example 12.
Figure 3C:
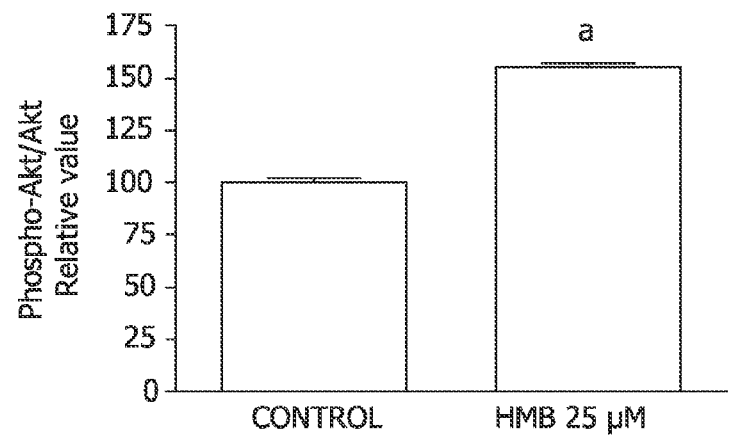
FIG. 3C is a graph depicting the effect of HMB on phosphorylative status of Akt in Neuro 2A cells as evaluated in Example 12.
Figure 4:
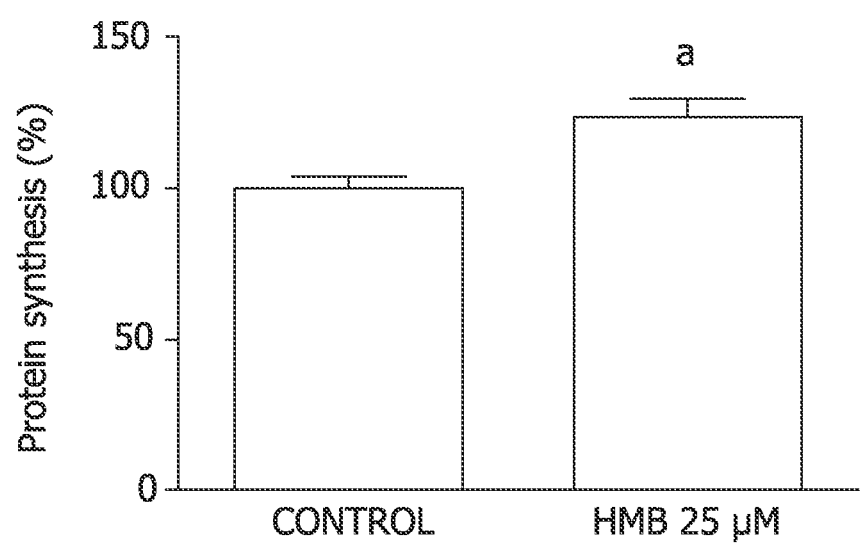
FIG. 4 is a graph depicting the effect of HMB on protein synthesis rate in Neuro 2A cells as evaluated in Example 12.

FIGS. 3A-3C shows the effect of HMB on the phosphorylation of mTOR and upstream regulators in Neuro 2A cells. Under the above-described cell culture conditions, HMB produced a significant increase in the phosphorylation of mTOR (FIG. 3A). Furthermore, HMB increased the phosphorylative status of Akt (FIG. 3C) and ERK 1/2 (FIG. 3B) in this cell line, which are the two main upstream regulators of the mTOR signaling pathway in mammalian cells. Moreover, the higher mTOR activation induced by HMB promoted an increase on the protein synthesis (20% HMB vs. Control, FIG. 4).

Figure 5A:
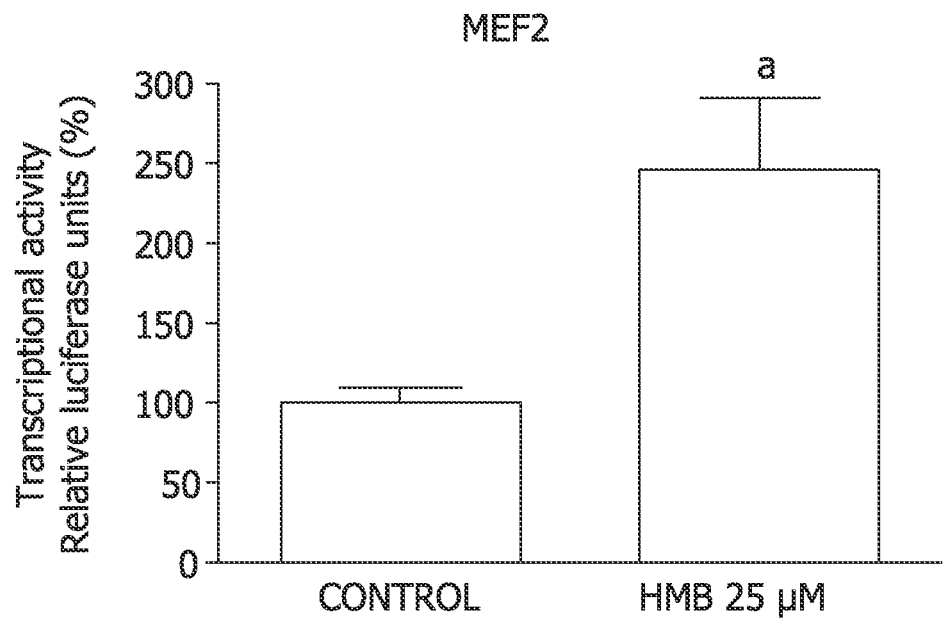
FIGS. 5A-5D are graphs depicting the effect of HMB on the expression of MEF2 transcription factor in Neuro 2A cells, in the absence or presence of different inhibitors, as evaluated in Example 12.
Figure 5B:
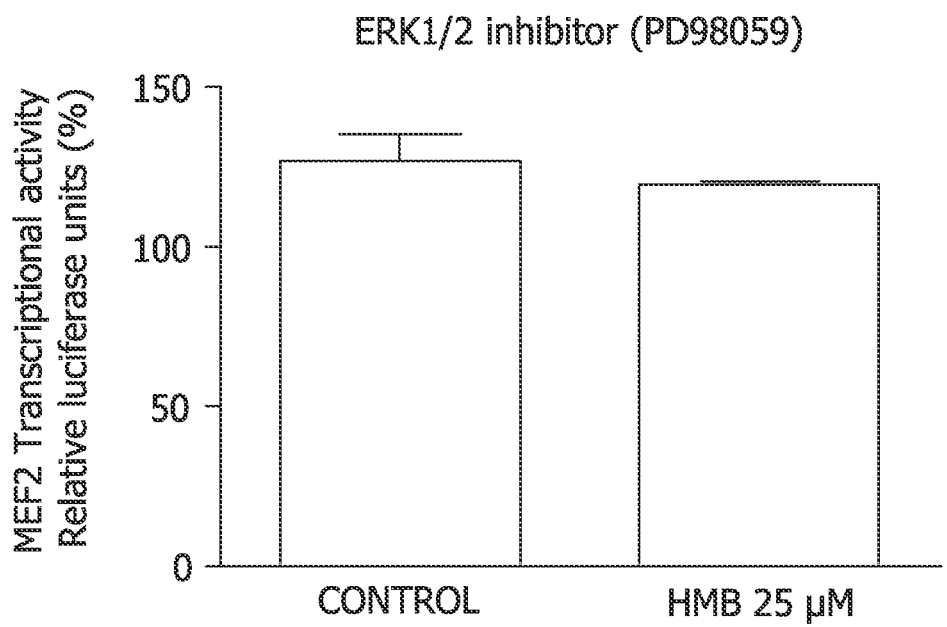
Figure 5C:
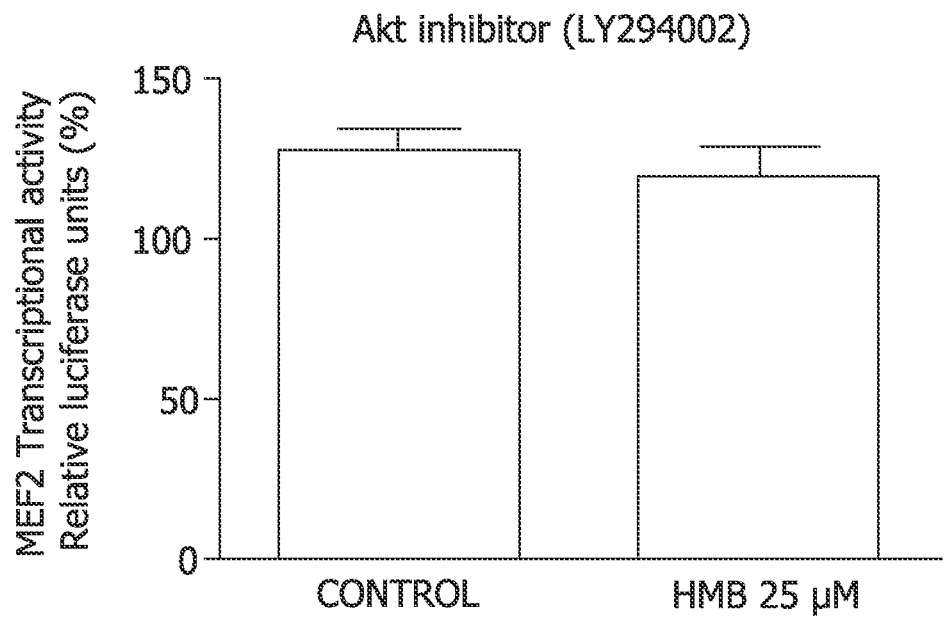
Figure 5D:
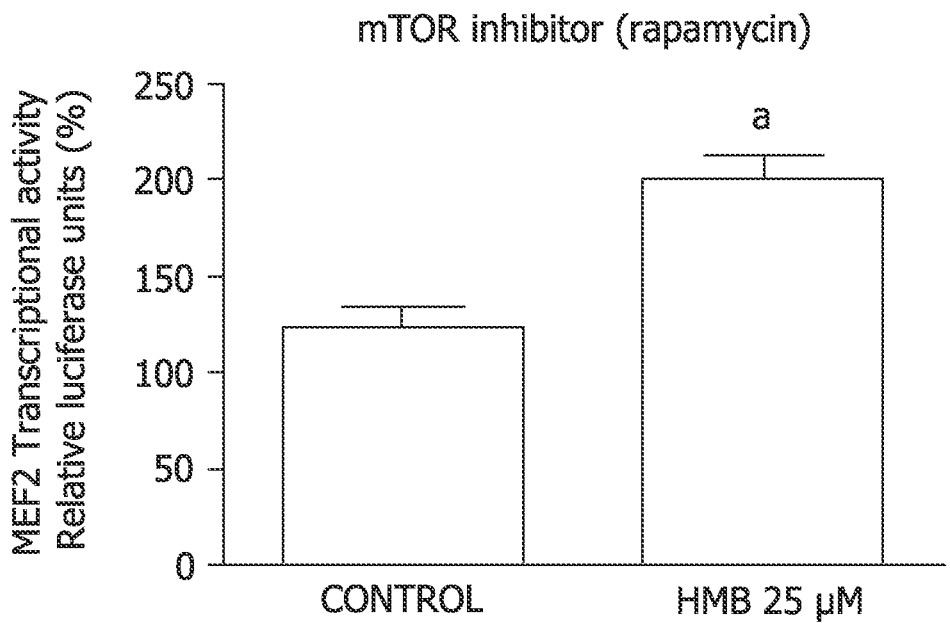

FIG. 5A displays the effect of HMB on the expression of MEF2 transcription factor in Neuro 2A. The supplementation of the media with HMB produced a significant increase in the MEF2-dependent transcription luciferase activity. The effects of LY294002, PD98059 and rapamycin inhibitors on MEF2 transcription factor are shown also in FIGS. 5B-5D. Either LY294002 or PD98059 totally blocked the HMB-mediated increase in MEF2. However, rapamycin had no effect on HMB-induced MEF2 expression. LY294002 and PD98059 act upstream of mTOR to block expression. This suppresses most, if not all, of mTOR activities. In contrast, rapamycin allosterically affects mTOR substrate interactions and selectively blocks only a subset of mTOR activities, those mediated by mTORC1 complex, but not others mediated by mTORC2. This is consistent with findings that rapamycin does not impede neuron survival, dendritic growth and complexity or action potentials targeted by PI3/AKT activation. The above-described data show that the Ras/ERK and PI3/AKT pathways may both be required for HMB-mediated MEF2 activity, placing MEF2 as a downstream effector of the Ras/ERK and PI3/AKT pathways.

Figure 6:
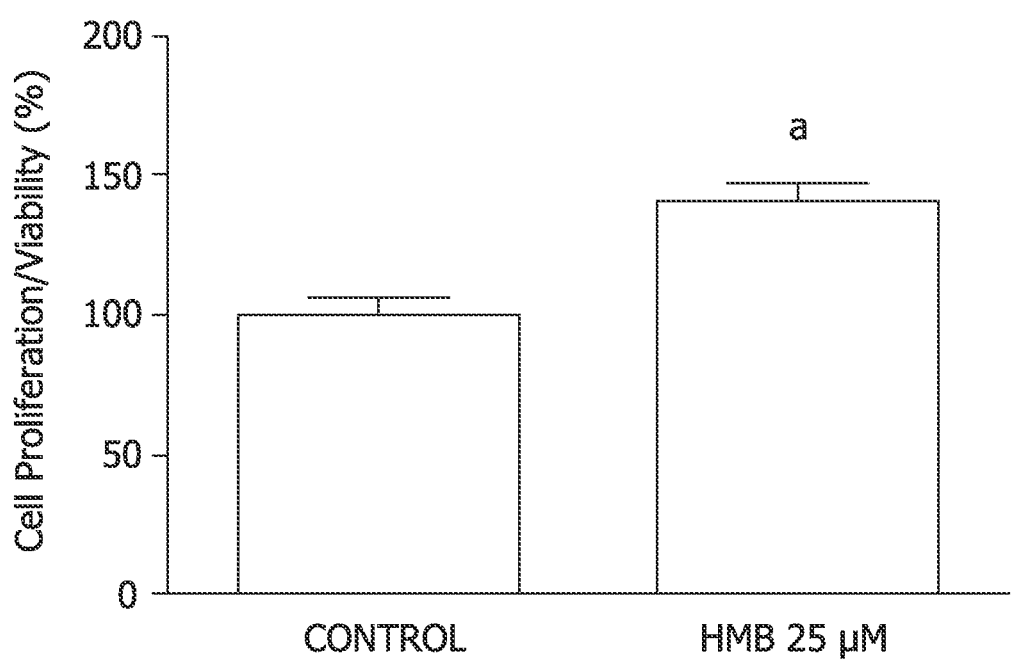
FIG. 6 is a graph depicting the effect of HMB on the proliferation and viability of Neuro 2A cells as evaluated in Example 12.

FIG. 6 shows the effect of HMB on neuronal proliferation and viability. As shown in FIG. 6, neuronal proliferation and viability were stimulated by HMB.

The data of this Example, using Neuro 2A cells, demonstrates that HMB acts as an effector able to modulate key signaling pathways such as mTOR-raptor/rictor-MEF2 that regulate key fundamental cell processes, such as protein synthesis and proliferation. Accordingly, HMB can assist in the development of the nervous system as well as for the management of neurodegenerative diseases by regulating neuronal signaling pathways.

Example 13

In this Example, the effect of HMB on anxiety/depression behavior in rats was analyzed.

This Example is based on the depression forced swimming test (FST) described by Porsolt, et al., 1978. To begin the experiment, rats were individually placed inside vertical cylinders (height: 40 cm; diameter: 21.5 cm) containing 30 cm of water at 25° C. for 15 minutes (i.e., "pre-swim"). Following this pre-swim period, the rats were removed and allowed to dry in a heated enclosure before returning to their cages. The rats were then orally administered a dose of either 250 mg/kg body weight or 500 mg/kg body weight HMB.

Twenty-four hours later, rats were submitted to the test swim, in which the rats were again placed in the cylinder for 5 minutes and the total duration of immobility and escape behaviors was evaluated. Test swims were videotaped and subsequently assessed for latency to immobility, which is the point at which no movements were observed and the rat was in the "deadman" position (i.e., head up, tail down, front legs slightly hunched, and rear legs pointed downwards). Rats were orally administered their respective doses of either 250 mg/kg body weight or 500 mg/kg body weight HMB four hours and one hour prior to the test swim.

Figure 7:
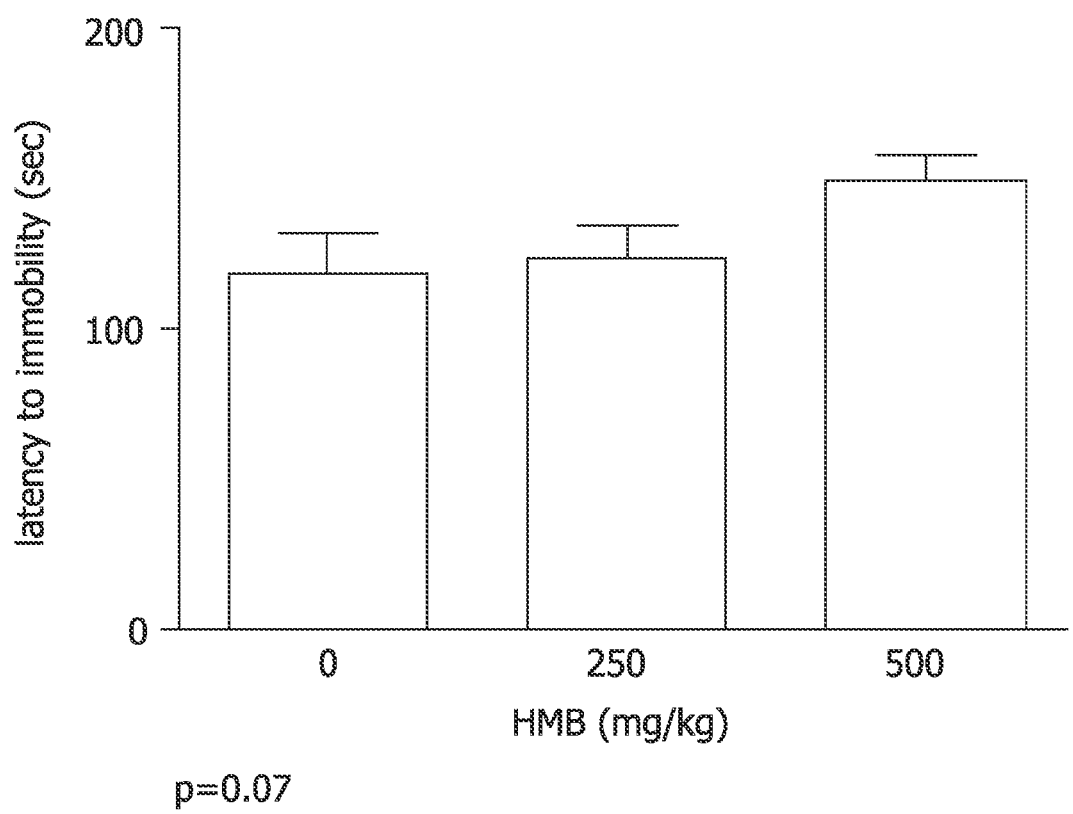
FIG. 7 is a graph depicting the anti-depression effect of HMB as measured by latency to immobility in a forced swim test as evaluated in Example 13.

As shown in FIG. 7, higher doses of HMB enhanced latency to immobility (P=0.07). This data indicates that administration of HMB has antidepressant-like effects.

What is claimed is:

1. A method for improving cognition in an older adult, the method comprising administering to the older adult a composition comprising an amount of beta-hydroxy-beta methylbutyrate effective to improve cognition in the older adult.

2. The method of claim 1 wherein the older adult is administered beta-hydroxy-beta-methylbutyrate daily.

3. The method of claim 2 wherein the older adult is administered from about 0.1 g/day to about 10 g/day of beta-hydroxy-beta-methylbutyrate.

4. The method of claim 2 wherein the older adult is administered from about 0.1 g/day to about 5.0 g/day of beta-hydroxy-beta-methylbutyrate.

5. The method of claim 1 wherein the composition is in a form selected from the group consisting of a nutritional powder, a nutritional emulsion, and a clear liquid.

6. The method of claim 1 wherein the older adult is suffering from cognitive decline.

7. The method of claim 1 wherein the older adult is suffering from neural dysfunction.

8. The method of claim 1 wherein the beta-hydroxy-beta methylbutyrate is administered for a period of at least one year.

9. A method for treating a cognitive disease associated with a neurodegenerative disease in an older adult, the method comprising administering to the older adult a composition comprising an amount of beta-hydroxy-beta methylbutyrate effective to treat the cognitive disease in the older adult.

10. The method of claim 9 wherein the neurodegenerative disease is selected from the group consisting of Alzheimer's disease, Huntington's disease, and Parkinson's disease, dementia, amyotrophic lateral sclerosis, stroke, and schizophrenia.

11. The method of claim 9 wherein the older adult is administered beta-hydroxy-beta-methylbutyrate daily.

12. The method of claim 11 wherein the older adult is administered from about 0.1 g/day to about 10 g/day of beta-hydroxy-beta-methylbutyrate.

13. The method of claim 11 wherein the older adult is administered from about 0.1 g/day to about 5.0 g/day of beta-hydroxy-beta-methylbutyrate.

14. The method of claim 9 wherein the composition is in a form selected from the group consisting of a nutritional powder, a nutritional emulsion, and a clear liquid.

15. A method for improving cognitive function in a toddler, child, or adolescent, the method comprising administering to the toddler, child or adolescent a composition comprising an amount of beta-hydroxy-beta-methylbutyrate effective to improve the cognitive function of the toddler, child, or adolescent.

* * * * *